United States Patent [19]
Gerber et al.

[11] Patent Number: 6,023,983
[45] Date of Patent: Feb. 15, 2000

[54] MACHINE FOR EXCISING A SPECIMEN OF ROCKET PROPELLANT

[75] Inventors: Robert L. Gerber; Norman G. Zweirzchowski, both of Ridgecrest; Herbert P. Richter, Oceanside; Larry R. Boyer, Inyokern, all of Calif.

[73] Assignee: The United States of America as represented by the Secretary of the Navy, Washington, D.C.

[21] Appl. No.: 09/076,987

[22] Filed: May 13, 1998

[51] Int. Cl.$^7$ ........................................ G01N 1/04
[52] U.S. Cl. ........................................ 73/864.41
[58] Field of Search ........................................ 73/864.41

[56] References Cited

U.S. PATENT DOCUMENTS

| | | | |
|---|---|---|---|
| 4,866,995 | 9/1989 | Kaiser et al. | 73/864.41 |
| 5,103,684 | 4/1992 | Denton | 73/864.41 |

*Primary Examiner*—Robert Raevis
*Attorney, Agent, or Firm*—David S. Kalmbaugh; Gregory M. Bokar

[57] ABSTRACT

A machine performs in situ excision of a specimen of tough and highly elastic solid propellant from a fin of the propellant disposed within a cavity extending from the nozzle opening of a rocket motor. The machine is mounted at the opening and has a rod extended into and moved generally axially of the cavity by an actuator assembly. A knife is mounted at one side of the rod end within the chamber. A mounting assembly supports the actuator assembly on the rocket motor and provides selective positioning of the actuator assembly axially of the cavity, of the angle of rod movement to the cavity axis, and of the knife position rotationally within the cavity. The actuator assembly has a guide received in the mounting assembly. The rod extends through the guide which prevents rotation of the rod while guiding it axially. From the guide, the rod extends successively to and through an air cylinder and a hydraulic dampening cylinder to a rod end bearing an adjustable stop for selecting the axial movement of the rod. A valve selects the degree of hydraulic dampening. Preferably, the knife is stirrup-shaped with a cutting edge facing either direction axially of the rod, and the air cylinder is double acting. Cuts may be thus made by extending or retracting the rod with a force and rate selected by the pressure applied to the air cylinder and by the degree of hydraulic dampening.

5 Claims, 4 Drawing Sheets

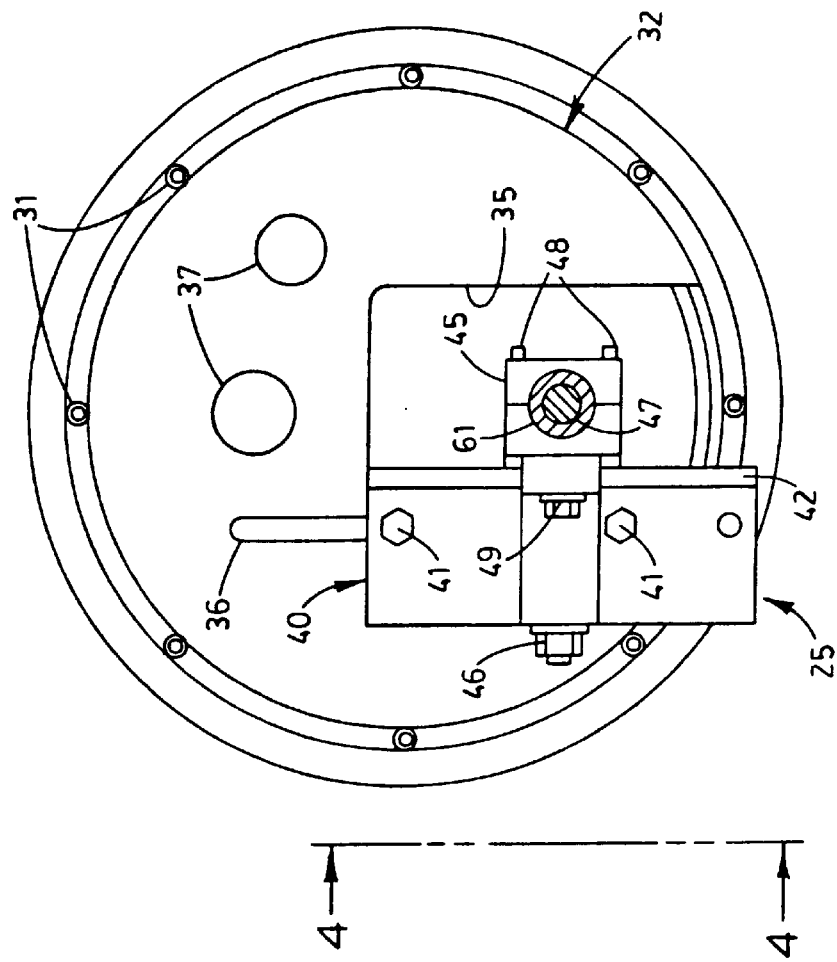
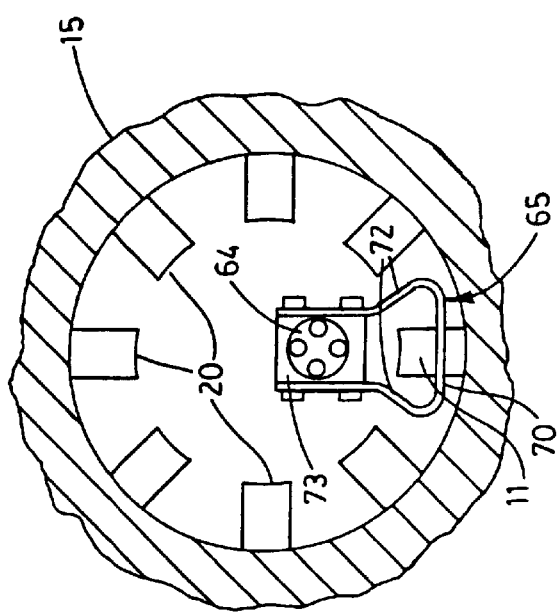

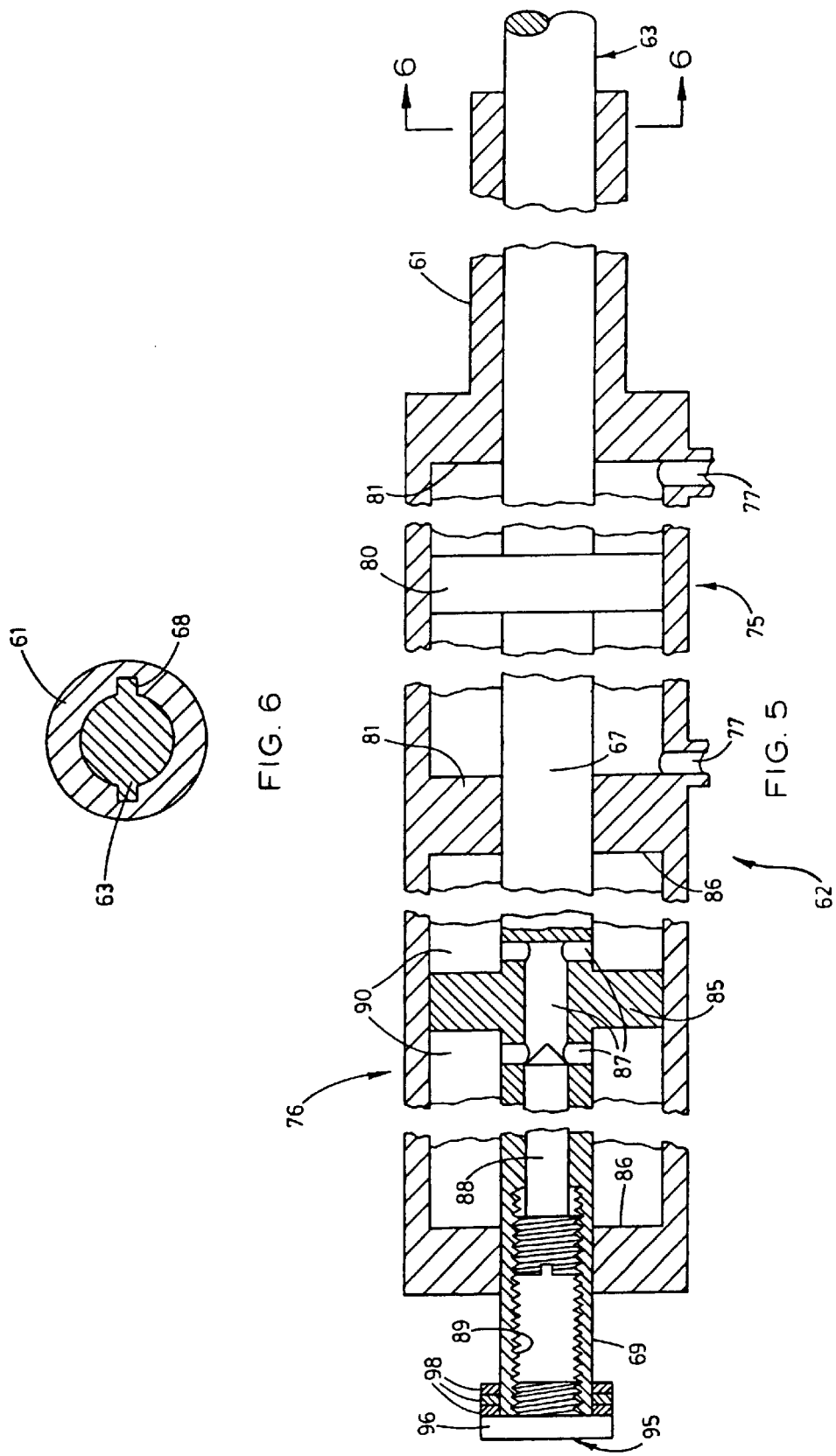

MACHINE FOR EXCISING A SPECIMEN OF ROCKET PROPELLANT

BACKGROUND OF THE INVENTION

1. Field of the Invention

The present invention pertains to devices for cutting elastomeric materials; and, more particularly, pertains to such devices for in situ sampling of specimens of solid propellant in rockets.

2. Description of the Prior Art

Large, military, solid propellant, rocket motors must be stored for decades and yet function with full effectiveness. To ensure this effectiveness, samples of the propellant may be taken regularly from substantially complete serviceable or specimen motors for testing to determine if the propellant has remained stable. The propellants of interest are elastomers which are very tough and highly elastic so as to retain their shape and function despite shocks in transportation and the intense vibrations and thermal stresses that occur following ignition. The propellant is, typically, a single large "grain" cast within a generally cylindrical casing having a smaller nozzle opening at one end from which a central cavity extends axially into the grain. This grain may include "fins" disposed circumferentially about and extending axially within the cavity.

Such tough and highly elastic propellants are difficult to cut since they compress rather than sever when subjected to a pressure from a cutting edge and since their elasticity induces oscillations when subjected to such pressure. Further, the necessary samples may be required from regions deep within the cavity and may require cuts along planes not parallel to the axis of the cavity.

Because of the mechanical properties of such elastomeric propellants, the large size of the motors and samples, and the relative inaccessibility of the propellant through the cavity, there has been heretofore no satisfactory remotely controlled, powered device for obtaining the necessary specimens; and the hazard to personnel resulting from ignition or detonation due to cutting energetic materials has been accepted by excising specimens of such propellant fins manually by a spade-like cutting device.

BRIEF SUMMARY OF THE INVENTION

Accordingly, an object of the present invention is to provide for the excision, without danger to personnel, of specimens from a fin or surface of solid propellant disposed within a rocket motor cavity.

Another object is to provide for such excision of such specimens from solid propellant which is very tough and highly elastic.

Still another object is to provide for such excision of such specimens which are well within the cavity and for such excision by cuts along planes not parallel to the axis of the cavity.

Yet another object is to provide for such excision through the nozzle opening of a rocket motor casing by a machine which may be conveniently mounted on the casing and which provides precise control of the rate and force of cutting.

Further objects are to provide improved elements and arrangements thereof in a machine which is fully effective for excising a specimen of rocket propellant.

These and other objects and advantages are provided by a machine for excising a specimen from a fin or surface of rocket propellant disposed within a generally cylindrical cavity extending from the nozzle opening of a rocket motor casing into a mass of the propellant. Typically, the fin from which the specimen is to be taken extends radially inwardly of and axially along the cavity between two circumferential stress relieving grooves in the propellant. The machine has a stirrup-shaped knife having a cutting edge which may face in either direction axially of the cavity. The knife is positioned in one of the stress relieving grooves, and the machine detaches the specimen by a cut passing through the fin or surface generally axially of the cavity to the other such groove.

The knife is mounted at one side of an end of a rod which is driven for extension or retraction in a direction generally along the cavity axis. The rod is mounted in an elongated actuator assembly and extends through a guide thereof which prevents rotation of the rod while guiding the axial movement of the rod. From the guide, the rod extends oppositely of its knife mounting end through a double acting air cylinder and then through a hydraulic dampening cylinder, the rod terminating outside the latter cylinder at a rod end bearing an adjustable stop for selectively limiting the axial movement of the rod.

The machine has a mounting assembly adapted for connection to the rocket motor casing across the nozzle opening. The mounting assembly receives the guide of the actuator assembly for selective positioning thereof along the cavity axis. The mounting assembly is also adapted for selective positioning of the guide across the cavity, for selection of the angle of the rod relative to the cavity axis, and for selection of the position of the knife rotationally within the cavity. The selective positioning provided by the mounting assembly allows the knife to be positioned for a desired cut location and plane in rocket motors having a wide range of cavity and fin configurations.

The distance of rod movement for the final cut is determined by the adjustable stop; and a valve within the dampening cylinder selects the degree of dampening to prevent axial oscillations of the rod during cutting. The cut may be made by either extending or retracting the rod by selecting the air cylinder end to be pressurized; and the force and rate of the final cut are selected by the pressure applied to the air cylinder and by the degree of hydraulic dampening.

BRIEF DESCRIPTION OF THE SEVERAL VIEWS OF THE DRAWING

FIG. 2 is a view from the position of line 2—2 of FIG. 1 and at a slightly enlarged scale showing a stirrup-shaped knife of the machine positioned for excising a specimen from a fin of rocket propellant.

FIG. 3 is a view from the position of line 3—3 of FIG. 2 and at a slightly enlarged scale showing elements of the machine for mounting it in a desired relation to a rocket motor.

FIG. 5 is a schematic, axial section of an actuator assembly of the machine, successive axial portions of the assembly being represented as omitted for illustrative convenience.

FIG. 6 is a schematic, diametric section of the assembly at line 6—6 of FIG. 5.

DETAILED DESCRIPTION OF THE INVENTION

Figure 1:
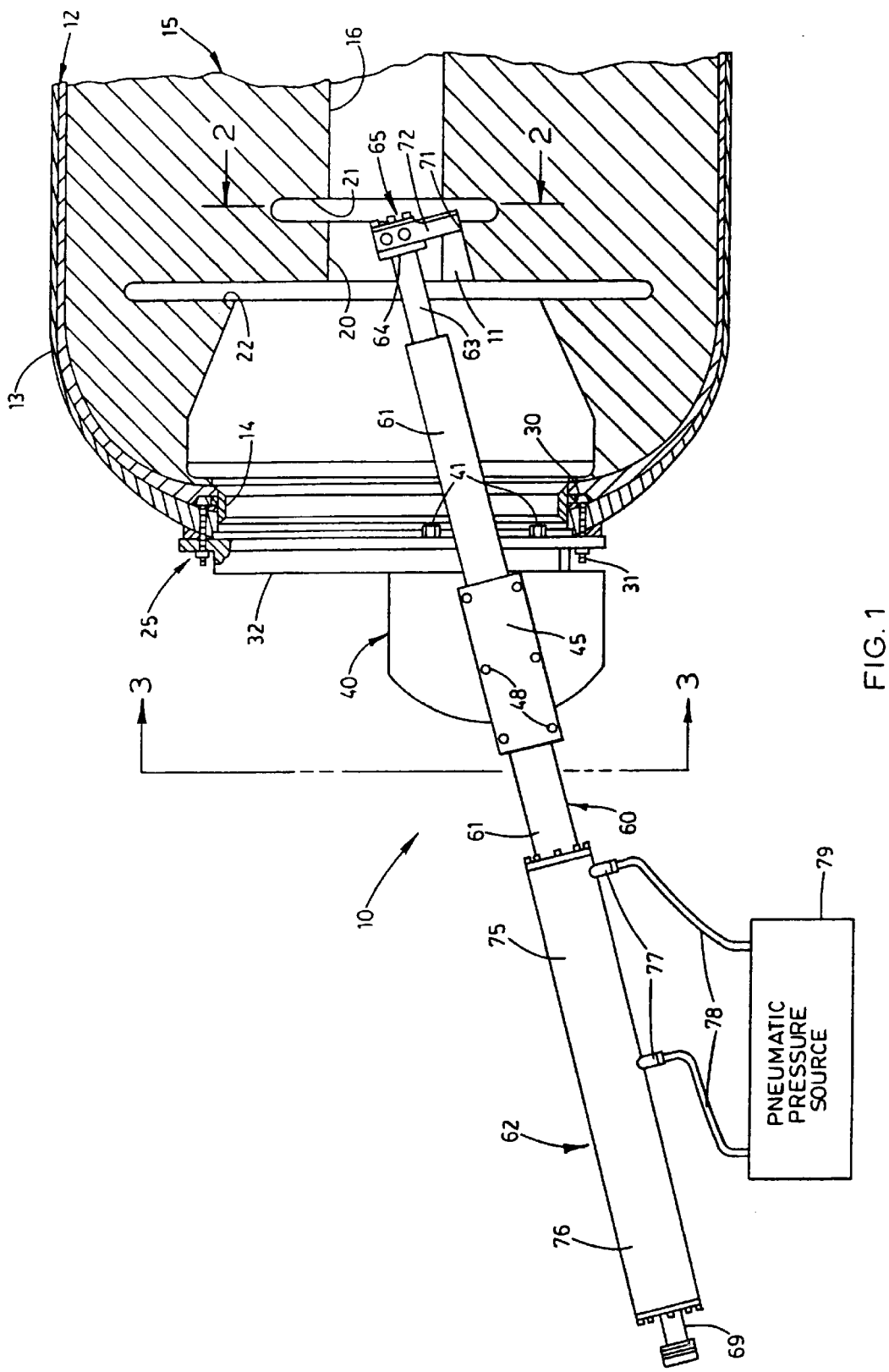
FIG. 1 is an elevation of a machine embodying the principles of the present invention for excising a specimen of rocket propellant, the machine being shown in operating relation to a representative and fragmentarily represented rocket motor.

Referring more particularly to FIGS. 1–3, numeral 10 indicates a machine embodying the principles of the present invention for excising a specimen 11 of elastomeric rocket propellant material from a rocket motor 12 of representative construction. The motor, as before stated, has a generally cylindrical casing 13 having a circular nozzle opening 14 at one axial end, and the propellant is a single mass or grain 15 cast within the casing and having a central, cylindrical cavity 16 extending axially into the grain.

Such a grain 15 to which the machine 10 is particularly adapted has projections or fins 20 disposed circumferentially about and extending axially within cavity 16 between circumferential stress relieving grooves, a forward groove 21 and a rearward groove 22 disposed at planes positioned transversely of the cavity. As best shown in FIG. 2, the fins extend radially inwardly into the cavity and specimen 11 is excised from one of the fins.

In order to excise specimen 11 from a desired location of grain 15, machine 10 is releasably attached to rocket motor 12 at its opening 14 by any suitable arrangement, such as that indicated in FIGS. 1 and 3 by numeral 25, providing for positioning of the balance of the machine axially, rotationally, and angularly in relation to cavity 16.

Mounting arrangement 25 includes an annular interior plate 30 which is disposed at nozzle opening 14 and which is provided with bolts 31 disposed in circumferentially spaced relation about the opening. These bolts extend axially from rocket motor 12 and through a generally circular mounting plate 32 sometimes referred to in the claims as a "first mounting member". This plate extends across the nozzle opening and is releasably attached to the motor by the bolts. This plate has a generally rectangular opening 35 for access of machine 10 to excise specimen 11, has a bolt slot 36 extending alongside this rectangular opening, and has windows 37 for viewing the position of elements of the machine within cavity 16.

Figure 4:
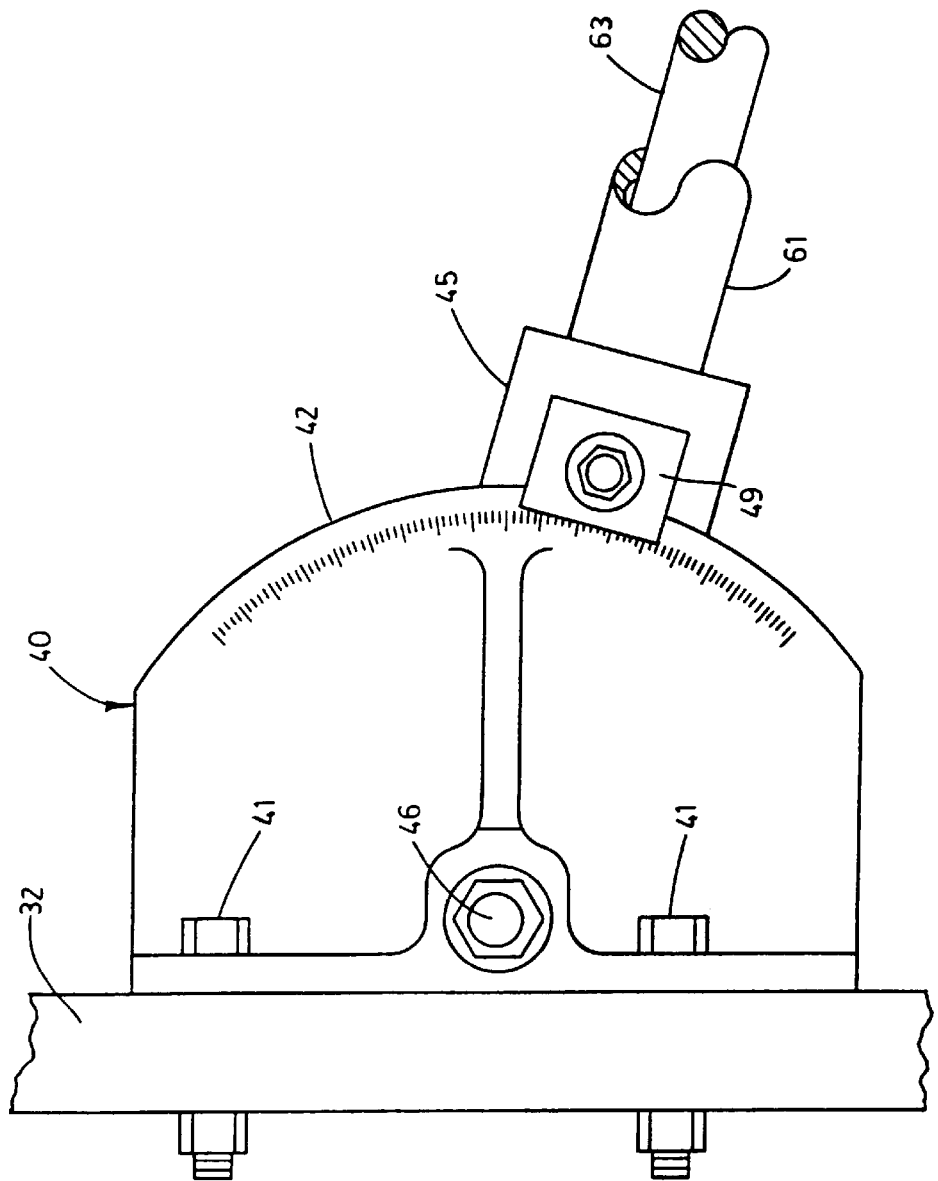
FIG. 4 is a view showing certain of the mounting elements from the position of line 4—4 of FIG. 3 and at an enlarged scale.

Arrangement 25 includes a pivot plate 40 shown in FIGS. 1, 3, and 4 and slidably mounted on mounting plate 32 at slot 36 for movement generally radially of nozzle opening 14. The pivot plate is releasably secured to the mounting plate by pair of bolts 41 extending through the pivot plate and the slot. The pivot plate extends from the mounting plate oppositely of the nozzle opening and is disposed at one side of access opening 35 in a plane disposed generally radially of the nozzle opening and terminates in a sector 42 bearing angle indicia.

Arrangement 25 also includes a clamp box 45 which is sometimes referred to in the claims as a "second mounting member". This box is disposed before access opening 35 at one side of the pivot plate 40 and is provided with movement angularly in relation to the axis of cavity 16 by a pivot 46 which is adjacent to the mounting plate 35 and extends through the pivot plate. The clamp box has a bore 47 parallel to the pivot plate and is split in a plane diametrically related to this bore, the split portions of the box being held in clamping relation by bolts 48. The clamp box is elongated axially of its bore and extends beyond the sector 42 where the box bears a clamp 49 for selecting the pivotal position of the box as indicated by the indicia on the sector. In FIGS. 1 and 4 this position is such that bore 47 is at an angle to the axis of cavity 16, while in FIG. 3 this bore is generally parallel to and disposed below the cavity axis.

As best shown in FIG. 1, machine 10 has an operating unit 60 which is subsequently described in detail and extends along and defines an operating axis of the machine. This unit includes a cylindrical guide 61 which extends through bore 47 of clamp box 45, an actuator assembly 62 which is mounted on the guide oppositely of the clamp box from rocket motor cavity 16, and an extensible and retractable rod 63 which extends from the guide into the cavity and there terminates in a distal end 64 bearing a knife 65 which moves with the rod and which is stirrup shaped as shown in FIG. 2. The rod is slidably mounted within the guide and extends axially thereof to the actuator assembly which motivates and controls the rod in movement along the machine axis. The rod has an actuator portion 67 shown in FIG. 5, this portion extending from the guide oppositely of the distal end of the rod 64 and through the actuator assembly. Rotational movement of the rod relative to the guide is prevented in any suitable manner, as by a keyway arrangement 68 shown in FIG. 6. The rod actuator portion terminates in a tail portion 69 extending from the actuator assembly oppositely of the guide.

It is apparent that guide 61 and actuator assembly 62 are connected to rod 63, are spaced from its end 64, and guide and power the rod in longitudinal movement. It is further apparent that mounting arrangement 25 supports operating unit 60 at nozzle opening 14 and provides for the positioning of this unit so that knife 65 is adjacent to the location of specimen 11 in a fin 20, as shown in FIGS. 1 and 2, and so that subsequent longitudinal movement of the rod by the actuator assembly moves the knife through the fin and excises the specimen.

It is evident that, when machine 10 is disposed as shown in FIGS. 1–4, guide 61 is directed generally longitudinally of rocket motor cavity 16 with clamp box 45 disposed centrally of the guide and with this box and pivot plate 40 connecting the guide and mounting plate 32 for relative pivotal movement to select the angle of rod 63 relative to the axis of cavity 16 and for relative slidable and longitudinal movement of the guide in the clamp box. After selecting the relative pivotal and longitudinal position of the guide relative to the mounting plate, this position is maintained by tightening bolts 48 and clamp 49.

Mounting arrangement 25 also provides for selective positioning of operating unit 60 transversely of nozzle opening 14 by slidable movement of pivot plate 40 on mounting plate 32 to a desired position maintained by bolts 41. The entire operating unit can be positioned rotationally in relation to rocket motor cavity 16 by relative movement between casing 13 and the mounting plate with a selected position maintained by tightening bolts 31. Since rod 63 cannot rotate relative to guide 61, the rotational position of knife 65 within the cavity can be selected, as when the longitudinal position of the guide is selected, by rotating the guide in clamp block bore 47, the selected rotational and longitudinal position being maintained by tightening bolts 48.

A feature of machine 10 is the construction of knife 65 for cutting the tough and highly elastomeric propellant of grain 15. As seen in FIGS. 1 and 2, the knife is of unitary construction and has a blade section 70 which extends tangentially of rod 63 and is spaced radially therefrom. This section has a cutting edge 71 facing along the rod and disposed, as shown in FIG. 1, for excising specimen 11. The knife has a pair of support sections 72 each joined at one end to one of the opposite ends of the blade section and extending therefrom to the distal end 64 of the rod. The other ends of the support sections are secured to this distal end diametrically oppositely thereof in any suitable manner as by a block 73 fixed by bolts to the rod end and to the knife.

As best shown in FIGS. 1 and 5, actuator assembly 62 has a power cylinder 75 fixed directly to guide 61 and has a dampening cylinder 76 fixed to the guide by being fixed to the power cylinder in axially adjacent relation thereto along actuator portion 67 of rod 63. These cylinders are disposed about this rod portion and may be of any suitable construction; therefore, constructional details such as seals, assembly arrangements, and fasteners well known in fluid power devices are omitted for clarity.

Power cylinder 75 has a pair of connections or ports 77 connected by hoses 78 to any suitable source 79 for providing air at a selected pressure to a selected one of the ports while providing an exhaust for the other port.

As shown in FIG. 5, power cylinder 75 has a piston 80 fixed to rod 63 centrally within the cylinder between a pair of cylinder heads 81 through each of which the rod extends in slidable, fluid sealed relation. One of the ports 77 opens into the power cylinder adjacently to each cylinder head for admitting pressurized air from source 79 to motivate the rod, together with knife 65, in a axial direction determined by which of the ports is selected for admission of pneumatic pressure.

Dampening cylinder 76 is similarly constructed and has a piston 85 fixed to rod 63 centrally between a pair of cylinder heads 86, one of which is combined with a power cylinder head. However, the dampening cylinder has no external connections, but has a selectively variable connection provided across its piston by ports 87 and a needle valve 88 which are disposed in the rod. In the depicted construction, a port extends diametrically through the rod on each side of this piston, and these diametrical ports are connected by a port extending along the rod axis and receiving a conical end of the valve. The opposite end of the valve is slotted and is engaged with a screw-threaded bore 89 extending axially within the rod and opening at the tail portion 69 thereof for access to adjust the valve.

Dampening cylinder 76 thus contains regions 90 between its piston and its heads, and these regions, together with ports 87, are filled with any suitable hydraulic dampening fluid, not specifically depicted. This fluid flows through these ports at a rate determined in a well-known manner by the axial position of needle valve 88 along bore 89 so that, while excising specimen 11 from the elastomeric propellant forming grain 15, this fluid flow rate controls the longitudinal speed of knife 65 and dampens oscillations in this movement due to the elastic properties of the propellant.

Rod actuator portion 67 includes a plug 95 screwthreadably engaging and closing bore 89, and this plug has a head 96 extending radially from the tail portion 69 of rod 63. A plurality of washers 98 having a selected combined thickness are disposed about this rod portion for engagement between the head of the plug and the adjacent dampening cylinder head 86. The plug and washers thus function as an adjustable stop mounted on the rod tail portion and selectively positionable along the rod to limit the movement of the rod along its axis in a direction toward rocket motor 12.

Although the machine has been shown and described in what is conceived as the preferred embodiment, it is to be understood that the invention may be practiced within the scope of the following claims other than as specifically set forth herein.

What is claimed is:

1. A machine for excising a specimen from a projection extending from a mass of elastomeric material, the machine comprising:
    a rod having an end;
    actuator means connected to the rod and spaced from said end for guiding the rod in longitudinal movement and for powering the rod in said longitudinal movement;
    a knife mounted on said end;
    said actuator means including a damper for oscillations of said longitudinal movement of the rod; and
    mounting means for supporting the actuator means and for positioning the actuator means to place the knife adjacent to the projection so that subsequent longitudinal movement of the rod by the actuator means moves the knife in a direction through the projection.

2. The machine of claim 1:
    wherein the mass of material is disposed within a casing having an opening, the mass of material defines a generally cylindrical cavity extending from the opening in the casing, and the projection extends radially inwardly of the cavity;
    wherein the rod extends from the actuator means; and wherein said mounting means is for supporting the actuator means at the opening so that the rod extends into the cavity with the knife disposed at the projection.

3. A machine for excising a specimen of elastomeric material from a quantity of the material disposed in a casing having a opening from which a generally cylindrical cavity extends into the material the specimen being taken from a portion of the material extending axially within the cavity between planes disposed transversely of the cavity, and the machine comprising:
    a first mounting member adapted to extend across the opening;
    means for releasably connecting the first mounting member to the casing;
    an elongated guide extended along a machine axis directed generally longitudinally of the cavity when the first mounting member is connected to the casing;
    a second mounting member disposed centrally of said elongated guide and connecting the first mounting member and the guide for relative pivotal movement so as to select the angle of said machine axis relative to the cavity, and for relative slidable movement along said machine axis;
    a rod slideably mounted in the guide for movement along the machine axis with rotational movement of the rod about the machine axis prevented, the rod having a distal end extended from the guide into the cavity and having an actuator portion extended from the guide oppositely of the distal end;
    a knife mounted on said distal end of the rod for movement with the rod along the machine axis;
    a power cylinder fixedly mounted on the guide about the actuator portion of the rod, said power cylinder having a power piston fixed to the rod centrally of the power cylinder, a pair of power cylinder heads disposed oppositely of the power piston with the rod extending in slidable, pressure sealed relation though each of said power cylinder heads, and a pair of pressurized fluid connections, one of said connections being adjacent to each of said power cylinder heads;
    a dampening cylinder fixedly mounted on the guide in axially adjacent relation to the power cylinder and about the actuator portion of the rod, said dampening cylinder having a dampening fluid, a dampening piston fixed to the rod centrally of the dampening cylinder, a pair of dampening cylinder heads disposed oppositely of the dampening piston with the rod extending in slidable, pressure sealed relation though each of said dampening cylinder heads, and a selectively variable connection for flow of said dampening fluid across the dampening piston;

pressurized fluid source means for providing a power fluid at a selected pressure to a selected one of said pressurized fluid connections for motivating said rod in a selected direction along said machine axis in movement dampened by said flow of said dampening fluid.

4. The machine of claim 3 wherein the knife is of unitary construction and comprises:

a blade section extending tangentially of the machine axis and spaced radially from the rod, said blade section having a pair of opposite ends and having a cutting edge facing along said axis; and a pair of support sections, each of said support sections having a first end and a second end, the first end being joined to a corresponding one of said opposite ends of the blade section, and the second end being fixed to the distal end of the rod diametrically oppositely of the rod from the second end of the other of said support sections.

5. The machine of claim 3 wherein the rod has a tail portion extending oppositely of the guide beyond the power cylinder and the dampening cylinder, and wherein the machine further comprises a stop mounted on said tail portion for selective positioning of the stop along the rod so as to limit the movement of the rod along the machine axis.

* * * * *